United States Patent
Stiefel et al.

(10) Patent No.: US 6,656,509 B1
(45) Date of Patent: Dec. 2, 2003

(54) COMBINATION OF SELENIUM-CONTAINING COMPOUNDS WITH CYTOSTATICS

(75) Inventors: Thomas Stiefel, Stuttgart (DE); Helmut Röhrer, Breisach (DE)

(73) Assignee: Biosyn Arzneimittel GmbH, Fellbach (DE)

( * ) Notice: Subject to any disclaimer, the term of this patent is extended or adjusted under 35 U.S.C. 154(b) by 0 days.

(21) Appl. No.: 09/701,326

(22) PCT Filed: May 31, 1999

(86) PCT No.: PCT/EP99/03771

§ 371 (c)(1),
(2), (4) Date: Nov. 27, 2000

(87) PCT Pub. No.: WO99/64018

PCT Pub. Date: Dec. 16, 1999

(30) Foreign Application Priority Data

Jun. 9, 1998 (DE) .......................... 198 25 746

(51) Int. Cl.⁷ .................. A61K 33/24; A61K 31/44; A61K 31/335; A61K 31/28

(52) U.S. Cl. .................. 424/617; 424/649; 514/283; 514/449; 514/492

(58) Field of Search .................. 424/617, 649; 514/449, 283, 492

(56) References Cited

U.S. PATENT DOCUMENTS 5,385,726 A   1/1995  Baldew et al.
5,783,454 A * 7/1998  Spallholz et al. ........... 436/525

FOREIGN PATENT DOCUMENTS

DE  40 24 885   2/1992
EP  0 750 911   1/1997

OTHER PUBLICATIONS

Choie et al., Toxicology and Applied Pharmacology, (1981) 60/2 (354–359) Abstract Only.*
Koepf–Maier et al., J of Cancer Research and Clinical Oncology, (1981) 102/1 (21–30) Abstract Only.*
Berry et al., J Submicrosc Cytol Pathol, (1988) 20 (1), 59–66 Abstract Only.*
Doroshow et al., *Pharmacology and Therapeutics*, 47 (3), 359–370 (1990).
Gustafson et al., *Cancer Chemotherapy and Pharmacology*, 28 (3), 228–230 (1991).
Kiremidjian–Schumacher et al., *Biological Trace Element Research*, 33 (1), 23–35 (1992).
Kramer, *Deutsche Zeitschrift fur Onkologie*, 26 (3), 76–83 (1994).
Saltiel et al., *The Western Journal of Medicine*, 139 (3), 332–341 (1983).
Strama et al., *Zeitschrift fur Onkologie*, 29 (1), 24–25 (1997).

* cited by examiner

Primary Examiner—Jerome D. Goldberg
(74) Attorney, Agent, or Firm—Needle & Rosenberg, P.C.

(57) ABSTRACT

The present invention relates to the use of selenium and/or a derivative thereof in combination with one or more cytostatics.

Figure 1:
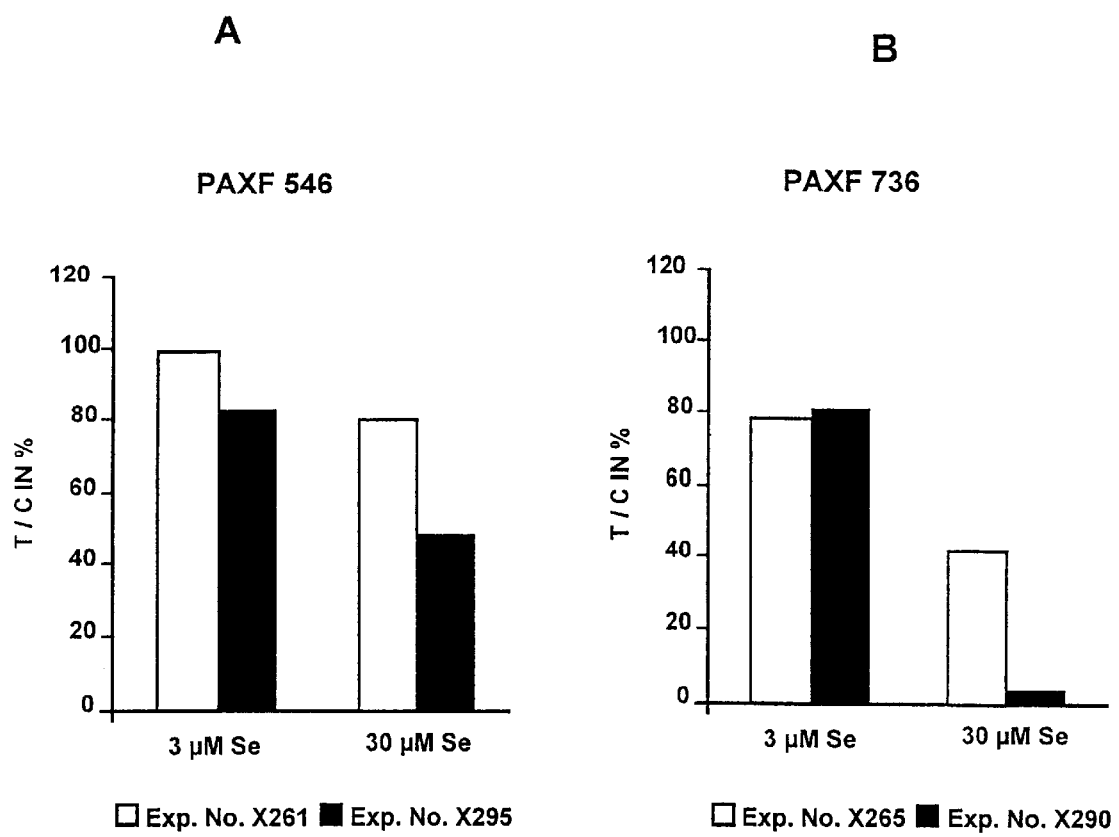

It is the object of the present invention to provide a possibility of enhancing the effect of antitumor drugs, and to provide said drugs in a suitable form of administration.

Said object is achieved by using selenium and/or at least one selenium compound for enhancing the effect of one or more cytostatics. This combination results in a synergistic, i.e. superadditive, enhancement of the effect. Furthermore, the present invention provides a kit containing selenium and/or at least one selenium compound and one or more cytostatics as a combination preparation for cytostatic therapy. The present invention can be used efficiently against various types of tumor cells, but especially against large-cell and small-cell bronchial carcinomas, adenocarcinomas, pancreatic carcinomas, prostatic carcinomas and hypemephromas.

7 Claims, 5 Drawing Sheets

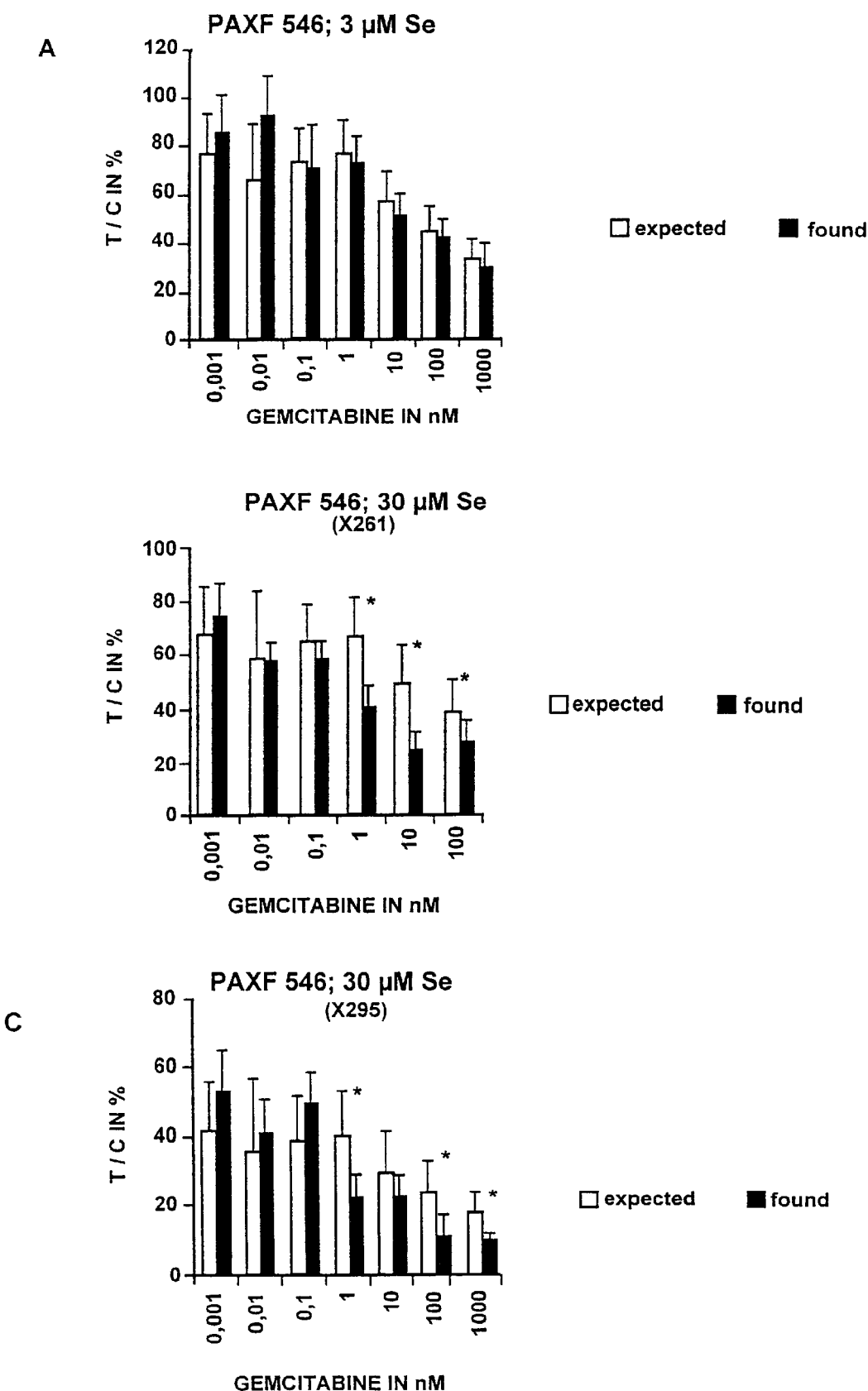

COMBINATION OF SELENIUM-CONTAINING COMPOUNDS WITH CYTOSTATICS

This application is a 371 of PCT/EP99/03771 filed May 31, 1999.

The present invention relates to the use of selenium and/or a derivative thereof in combination with a cytostatic or a mixture of cytostatics.

The chemical element selenium is a trace element which is essential for humans and animals and influences above all oxidative processes as well as thyroxine metabolism. In humans it could be detected that the enzyme glutathione peroxidase and the selenoprotein P found in plasma contain selenium in the form of the amino acid selenocysteine. The selenium-containing glutathione peroxidase forms part of the antioxidative protective system of the mammalian cell. In the presence of sufficient amounts of substrate, i.e. reduced glutathione, glutathione peroxidase converts a multitude of different hydroperoxides into corresponding alcohols. It could be demonstrated that the integrity of cellular and subcellular membranes decisively depends on the intactness of the glutathione peroxidase system. Selenium as part of glutathione peroxidase can reduce the lipid peroxidation rate and the resulting membrane damage.

In animals the type-I iodothyronine-5'-deiodase was recently characterized as a selenium-containing enzyme. In the thyroid, liver and lung of humans, iodothyronine deiodase also converts thyroxine ($T_4$) into triiodothyronine ($T_3$), the active thyroid hormone. In the case of selenium deficiencies, e.g. phenylketonuria and cystic fibrosis, increased $T_4$ values could be detected at a simultaneously reduced $T_3$ level. By the administration of sodium selenite ($Na_2SeO_3$) the thyroid metabolism is normalized again.

As a further selenium-dependent enzyme, a human thioredoxin reductase from lung cells was recently described to contain selenium as a cofactor (Tamura and Stadtman, 1996, Biochemistry, Proc. Natl. Acad. Sci., 93: 1006–101 1). The enzyme could so far be isolated from T cells, lung tissue and placenta (Gladyshev et al., 1996, Biochemistry, Proc. Natl. Acad. Sci., 93: 6146–6151). The selenium-dependent enzyme thioredoxin reductase reduces thioredoxin. Thioredoxin is overexpressed in a number of tumors, and some experimental studies have shown that thioredoxin contributes to the growth and malign transformation of some human cancer cells. The enzyme thioredoxin reductase therefore plays a role in the regulation of the growth of normal and cancer cells.

Proof of the pathophysiological relevance of the selenium-dependent reactions has been furnished by observation of selenium deficiency symptoms in humans and in animals. Deficiency of this trace element intensifies oxidatively or chemically induced liver damage and the toxicity of heavy metals such as mercury and cadmium.

In humans the Keshan disease, an endemically occurring cariomyopathy, and the so-called Kaschin-Beck disease, also an endemically occurring osteoathropathy with strong deformations of the joints, are described as selenium deficiency symptoms. Clinically manifested selenium deficiency was also observed as a consequence of long-term parenteral feeding and of balanced diets. Cardiomyopathies and myopathies of the skeletal muscles as well as a shift in the $T_3/T_4$ ratio were above all observed.

Epidemiological studies hint at an inverse correlation between blood-selenium level and the incidence of cardio-vascular diseases (cardiomyopathies, arteriosclerosis, myocardial infraction) and tumor diseases, in particular of the digestive system, breast and liver. Reduced selenium levels in plasma may be present in patients with renal insufficiency and in the case of gastrointestinal diseases. Selenium deficiency can be detected through a reduced selenium level in whole blood or plasma and a reduced glutathione peroxidase activity in whole blood, plasma or thrombocytes.

Selenium substitution in the case of deficiency symptoms activates reactions of the immune defense, in particular unspecific, cell-bound and humoral reactions. The selenium-containing glutathione peroxidase influences leukotriene, thromboxane and prostacyclin metabolism. The immuno-modulatory effects of selenium-containing compounds are listed in the following:

Stimulation of lymphocyte proliferation
Activation of cytotoxic T cells and NK cells
Increase in interleukin-2 receptor expression
Selective reduction of the number of T suppressor cells
Increase in interferon-γ synthesis
general decrease in infection frequency Selenium in the form of selenite ($SeO_3^{2-}$) is not directly incorporated into proteins. In blood, selenite is first mainly taken up by erythrocytes and enzymatically reduced to selenium hydrogen. Selenium hydrogen serves as a central selenium pool for excretion and for the targeted incorporation into selenoproteins. In this reduced form selenium is bound to plasma proteins which migrate into the liver and other organs. The plasmatic secondary transportation starting from the liver into the glutathione peroxidase-synthetized target tissue probably takes place in the form of a selenocysteine-containing P selenoprotein. The further metabolic course of selenoprotein biosynthesis has so far only been known from prokaryotic model organisms. In these organisms selenocysteine is specifically incorporated-into the peptide chain of the glutathione peroxidase in the course of the translation.

Excessive selenium hydrogen in humans is metabolized through methylselenol and dimethylselenide to trimethylselenonium ion, the main excretion product. After oral application selenite is predominantly absorbed from the small intestine. The intestinal absorption of sodium selenite is not regulated homeostatically. Depending on the concentration and on additives, it is between 44% and 89%, sometimes over 90%. The amino acid cysteine promotes the sodium selenite absorption.

Organic selenium compounds must first be converted into selenium hydrogen before they are available for the synthesis of selenoproteins. Instead of methionine, selenomethionine, which is mainly contained in food, can also be unspecifically incorporated statistically in the case of protein biosynthesis into proteins that do not contain selenium.

The total amount of selenium in the human body is between 4 mg and 20 mg in a well-balanced selenium metabolism. Selenium is excreted in humans via urine, faeces and lung, depending on the dose applied. Selenium is primarily excreted renally in the form of the above-mentioned trimethylselenonium ions.

In humans acute selenium intoxications have hardly been described up to now. Garlic-like breadth, tiredness, queasiness, diarrhea and abdominal pain are regarded as signs of an acute overdosage. In humans, a safe maximum daily intake of selenium of 820 μg was inferred from observations regarding the chronic toxicity of selenium, while a dosage of up to 500 μg per day is also considered to be harmless in sensitive persons. As clinical signs of endemically occurring selenosis, alopecia, brittleness of the finger nails, skin alterations and disorders in the nerve system were observed in a study carried out in China after a daily supply of 3200–6700 µg selenium. In various species a decreased reproductive capacity because of a reduced motility of spermatozoons was described as a symptom of selenosis.

In a dose/escalation study, between 10 and 50 mg selenium were infused in the form of sodium-selenite pentahydrate in tumor patients. Within 30 minutes the selenium level in plasma rose from 200 µg/l to 1200 µg/l after administration of 10 mg selenium as sodium selenite. After 8 and 16 hours the plasma selenium decreased to 770 µg/l and 430 µg/l, respectively. After 24 hours the selenium level in plasma had again reached its initial value. Gastrointestinal toxicity was observed starting from about 20 mg selenium as sodium selenite and was reversible after the administration of the preparation had been stopped (Röhrer H., 1989, Erfahrungsheilkunde 38: 10a, 761).

As counter-measures in the case of intoxication, gastric lavage, forced diuresis, or highly dosed vitamin C administrations are possible. In the case of an extreme overdosage (1000 to 10000 times), the attempt can be made to eliminate selenite by dialysis.

In humans, the trace element selenium is predominantly taken in by consumption of yolk, fish and meat, in particular chicken and pork, as well as innards. The minimum selenium supply required for humans depends on the chemical form of the consumed element and on the composition of the diet in which it is present. In China, experiments revealed an amount of 15–20 µg selenium a day to be sufficient as protection against endemic selenium deficiency diseases. The National Research Council (NRC) of the USA recommends a daily supply of 70 µg selenium for males and 55 µg selenium for females. In former times (up to 1989) the NCR regarded daily amounts of 50–200 µg selenium as adequate and harmless. The German Society for Alimentation recommends 20–100 µg selenium per day.

The daily average selenium supply, 2/3 covered by the supply of animal protein, is 38 µg for women and 47 µg for men in the old federal states of Germany. By contrast, in the territory of the new federal states of Germany, values of 20–25 µg selenium were determined. These figures demonstrate that the nutritive selenium supply in Germany is not always covered. The risk of an insufficient supply with selenium exists especially in situations of increased demands (e.g. pregnancy and lactation period), in persons exposed to heavy metals and oxidants, in patients with gastrointestinal complications (e.g. chronically inflammatory bowel diseases) and in parenterally fed persons or persons observing special diets (e.g. in the case of phenylketonuria).

Epidemiological studies have shown that a low selenium intake and correspondingly low selenium levels in plasma are connected with an increased incidence of a variety of cancers in humans (Glattre et al., 1989, Int. J. Epedemiol., 18:45–49; Knekt et al., 1990; J. Natl. Cancer Inst., 82:864–868; Burney et al., 1997, J. Clin. Nutr., 49:895–900). Selenium has also been shown to markedly inhibit the growth of different tumor cells in vitro in high dose levels (20–200 µM), including human mammary, ovarian and colon tumor cells. (Yan et al., 1991; Biol. Trace Elem. Res., 30:145–162; Chen et al., 1995, FASEB J., 9(3): A159; Nano et al., 1989, Biol. Trace Elem. Res. 20: 31–43; Stewart et al., 1997, Cancer Lett., 117:35–40). By contrast, several scientists reported on the growth stimulating effect of small amounts of sodium selenite (0.001–1 µM) on various tumor cells incubated under serum-free culture conditions (Nano et al., 1989, Biol. Trace Elem. Res., 20:31–43; Goiczewski and Frenkel, 1989, Biol. Trace Elem. Res. 20:115–126). It has also been observed that organic selenium compounds have a preventive effect on the tumor development of mammary carcinomas in mice and rats (El-Bayoumy et al., 1995, J. Cell. Biochemistry, Annex 22: 29–100). The mechanism by which selenium influences tumor proliferation or regression is mainly unknown. However, it seems that induction of DNA strand breaks and apoptosis due to selenium and/or selenium metabolites like selenodiglutathione and hydrogen selenite as well as the formation of selenoproteins such as glutathione peroxidase and thioredoxin reductase play an important role (Thompson et al., 1994, Carcinogenesis 15:183–186; Wu et al., 1995, Carcinogenesis 16: 1579–1584; Lu et al., 1994, Biochem. Pharmacol., 47:1531–1535; Milner, 1985, Fed. Proc., 44: 2568–2572; Schrauzer, 1992, Biol. Trace Elem. Res., 33:51–62; Gallegos et al., 1997, Cancer Res., 75:4965–4979). For example, enhancing thioredoxin reductase activity by selenium could reduce cellular thioredoxin concentration and therefore play a role in the growth regulation of cancer cells (Gallegos et al., 1997, Cancer Res., 75: 4965–4979).

In combination experiments it has been observed that the administration of small amounts of selenium or selenium-containing compounds together with cytostatics does not decrease the antitumor effect, but can considerably reduce the side effects caused by cytostatics, for instance nephrotoxicity or cardiotoxicity.

While quite efficient therapeutic methods could already be developed for some types of cancer (the mortality rate following colon cancer disease could e.g. be reduced by about 17% between 1992 to 1993), there has so far been no or only a very inadequate therapy for the great majority of types of cancer.

Apart from the operative removal of the tumor and radiation therapy, chemotherapy is considered the so far most efficient therapeutic method. Chemotherapeutic drugs can substantially be divided into the following four groups: antimetabolites, topoisomerase inhibitors, alkylating agents and plant alkaloids, the three first-mentioned groups preventing a correct replication of the genetic substance, and the last-mentioned group having a mitosis-inhibiting effect. In the treatment of above all solid tumors the effect of cytostatics is most of the time not sufficient for curatively treating tumors.

It is therefore the object of the present invention to provide a possibility of enhancing the effect of antitumor drugs and to provide said drugs in a suitable form of administration.

This object is achieved by using selenium and/or at least one selenium compound for enhancing the effect of a cytostatic or a mixture of cytostatics.

Furthermore, this object is achieved by providing a kit comprising selenium and/or at least one selenium compound and a cytostatic or a mixture of cytostatics as a combination preparation for simultaneous, separate or sequential application in cytostatic therapy.

The present invention relates to the use of selenium and/or at least one selenium compound for enhancing the effect of a cytostatic or a mixture of cytostatics. The following examples will demonstrate that in vitro a simultaneous treatment with the above-mentioned components surprisingly yields a distinct synergistic, i.e. superadditive, antitumor effect.

Organic and inorganic selenium compounds are used for combination with cytostatics. In a preferred embodiment use is made of an organic selenium compound. The use of organic selenium compounds is to reduce toxicity in comparison with inorganic selenium compounds with simultaneous or improved antitumor efficiency. Particularly preferred are the selenium amino acids selenomethionine and selenocysteine as well as the compound phenylenebis (methylene)selenocyanate as well as derivatives thereof (El-Bayonmi et al., 1995, *J. Cell. Biochemistry, Annex 22:* 92–100). The last-mentioned compound inhibits thymidine kinase in human mammary carcinoma cell lines. Furthermore, it has been reported that said compound can trigger the inhibition of cell growth and the induction of cell death by apoptosis.

Furthermore, a selenium oxide is preferred as the selenium compound for enhancing the effect of a cytostatic or a mixture of cytostatics. In a particularly preferred embodiment, the selenium compound is a salt of $SeO_2$, e.g. the salt $Na_2SeO_3$.

The cytostatic that is used together with selenium or a selenium compound may be a mitosis-inhibiting cytostatic. Examples of said group are inter alia substances, such as vinblastine and vinorelbine.

The cytostatic used together with selenium or a selenium compound may also be a cytostatic inhibiting nucleic acid synthesis, for example methotrexate and fluorouracil, which belong to the group of antimetabolites, or the topisomerase inhibitor topotecan, mRNA synthesis inhibitors such as doxorubicin, or alkylating agents such as cyclophosphamide and chlorambucil. The following table gives examples of different cytostatics, in the order of their modes of action, which are suited for administration together with selenium compounds. Combinations of several different cytostatics can also be used together with selenium compounds.

| Effect on | Mode of action | Groups of cytostatics and examples of substances | Dosage ranges |
|---|---|---|---|
| DNS | Enzyme inhibition | Antimetabolites | |
| bio-synthesis | -dihydrofolate reductase | ⇒Methotrexate | ⇒20–40 mg/m$^2$/d i.v. HD: 12 g/m$^2$ |
| | -thymidylate synthase | ⇒5-FU | ⇒500–600 mg/m$^2$ i.v. or 2–2,6 g/m$^2$ i.v. (24-h-inf) |
| | DNS polymerase | ⇒ZD1694 (Tomudex) | ⇒3 mg/m$^2$/d i.v. |
| | | ⇒Capecitabine | ⇒about 500 mg/m$^2$/d p.o. |
| | | ⇒Gemcitabine | ⇒1000–1250 mg/m$^2$ i.v. |
| | | ⇒Cytosine arabinoside | ⇒200 mg/m$^2$/d i.v. HD: 3 g/m$^2$ |
| | -ribonucleotide reductase | ⇒Hydroxy urea | ⇒800–1600 mg/m$^2$/d p.o. |
| | | ⇒6-mercaptopurine | ⇒100 mg/m$^2$/d p.o. |
| DNS | Induction of strand breaks | Alkylating agents | |
| | -intermediate strand cross-linkage | | |
| | -intercalation | Mustargen | ⇒6 mg/m$^2$ |
| | | Estramustine phosphate | ⇒480–550 mg/m$^2$/d p.o. 150–200 mg/m$^2$ i.v. |
| | | Melphalan | ⇒8–10 mg/m$^2$/d p.o. 15 mg/m$^2$/d i.v. |
| | | Chlorambucil | ⇒3–6 mg/m$^2$/d p.o. |
| | | Prednimustine | ⇒40 mg/m$^2$/d p.o. or 60–100 mg/m$^2$/d p.o. |
| | | Cyclophosphamide | ⇒750–1200 mg/m$^2$/d i.v. or 50–100 mg/m$^2$/d p.o. HD: 2,4 g/m$^2$ i.v |
| | | Ifosfamide | ⇒1500–2000 mg/m$^2$/d i.v. |
| | | Trofosfamide | ⇒150–200 mg/m$^2$/d p.o. initially then 25–100 mg/m$^2$ |
| | | Busulfan | ⇒2–6 mg/m$^2$/d p.o. |
| | | Treosulfan | ⇒5–8 g/m$^2$/d i.v. or 1500 mg/m$^2$/d p.o. ⇒12–16 mg/m$^2$ i.v. |
| | | Thiotepa | ⇒100 mg/m$^2$/d i.v. |
| | | Carmustine | ⇒100 mg/m$^2$ p.o. |
| | | Lomustine | ⇒90–100 mg/m$^2$ i.v. |
| | | Nimustine | ⇒100–200 mg/m$^2$/d i.v. |
| | | Dacarbazine | ⇒100 mg/m$^2$ p.o. |
| | | Procarbazine | ⇒1.5 mg/m$^2$ i.v. |
| | -Topoisomerase toxins | Topotecan | ⇒100–350 mg/m$^2$ i.v. |
| | | Irinotecan | |
| | | Platinum complexes | ⇒20 mg/m$^2$/d i.v. or 80–120 mg/m$^2$ i.v. |
| | | Cisplatin | ⇒300–400 mg/m$^2$ i.v. |
| | | Carboplatin | ⇒80–135 mg/m$^2$ i.v. |
| | | Oxaliplatin | |
| | | Antibiotics (see below) | |
| | | Epipodophyllotoxins | ⇒100–200 mg/m$^2$/d i.v. |
| | | Etoposide | ⇒20–30 mg/m$^2$/d i.v. |
| | | Teniposide | |

-continued

| Effect on | Mode of action | Groups of cytostatics and examples of substances | Dosage ranges |
|---|---|---|---|
| RNA | Blockage of mRNA synthesis by intercalation | Antibiotics Aclarubicin Bleomycin Actinomycin D (Dactinomycin) | ⇒25–100 mg/m² i.v. ⇒10–15 mg/m² i.v. ⇒0,6 mg/m²/d i.v. |
| | Incorporation in RNA | Daunorubicin Doxorubicin Epirubicin Idarubicin | ⇒45–60 mg/m²/d i.v. ⇒45–60 mg/m² i.v. ⇒60–80 mg/m² i.v. ⇒10–12 mg/m² i.v. or 35–50 mg/m² p.o. |
| | | Mitoxantrone Mitomycin C Antimetabolites (see above) | ⇒10–12 mg/m² i.v. ⇒10–20 mg/m² i.v. |
| Protein | Modifications of receptor bindings | Hormones & Antagonists Vitamin-A acid deriv. | |
| | | Tretinoin | ⇒45 mg/m² |
| | Inhibition of tubulin polymerization | Vinca alkaloids Vincristine Vindesine Vinblastine Vinorelbine Taxanes | ⇒1,5–2,0 mg i.v. ⇒2–3 mg/m² i.v. ⇒4–8 mg/m² i.v. ⇒25–30 mg/m² |
| | | Taxol (Paclitaxel) Taxotere (Docetaxel) | ⇒175 mg/m² i.v. ⇒100 mg/m² i.v. |
| | Protein cross-linkage Phosphorylation | Alkylating agents (see above) Protein kinase-C inhibitors Miltefosine | ⇒max. 5 ml/d, local application |

HD = high-dose therapy

A preferred cytostatic inhibiting nucleic acid synthesis is gemcitabine. A further, also preferred, cytostatic that inhibits nucleic acid synthesis is the compound mitomycin C. The structural formulae of said two compounds are shown in the following:

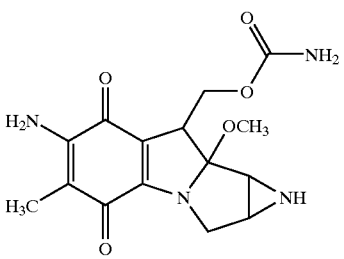

Mitomycin C

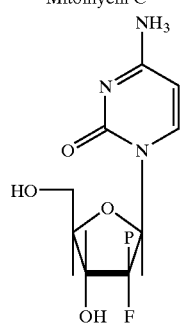

Gemcitabine

Mitomycin C belongs to the group of alkylating agents. Upon reduction of the quinone unit, methanol is released, which facilitates opening of the aziridine ring to form an alkylating metabolite. A further alkylating molecule is formed by chemical or enzymatic separation of the carbamate side chain. Moreover, the reduction of the quinone unit is connected with the formation of reactive oxygen molecules, which also have alkylating potency. The antitumor effect of mitomycin is mainly due to the alkylation of DNA.

Gemcitabine is a pyrimidine antimetabolite. After cellular uptake, it is metabolized to 2',2'-difluoro-deoxycytidinetnphosphate. Incorporation of gemcitabine into DNA terminates DNA strand synthesis, so that cell division is no longer possible.

Gemcitabine and mitomycin C have different modes of action, but both compounds interact directly with cellular DNA, leading to errors or discontinuance of DNA replication.

To enhance the effect of a cytostatic or the combination of several cytostatics, selenium and/or at least one selenium compound is used in a concentration of 0.1 mg/kg body weight to 1.25 mg/kg body weight, and the cytostatic is used in a concentration of 2 mg/M² body surface to 240 g/m² body surface. The preferred concentration of selenium or a selenium compound is in a range of 0.1 mg/kg body weight to 0.3 mg/kg body weight, and that of the cytostatic is in a range of 20 mg/M² body surface to 1000 mg/m² body surface.

The use of said combination in cytostatic therapy is particularly preferred.

Furthermore, the invention provides a kit which comprises selenium and/or at least one selenium compound and a cytostatic or a mixture of cytostatics as combination preparation for simultaneous, separate or sequential application in cytostatic therapy. It is preferred that the selenium compound contained in the kit is an organic selenium compound. Particularly preferred organic selenium compounds are the selenium amino acids selenomethionine and selenocysteine as well as the compound phenylene-bis (methylene)selenium cyanate. Moreover, a selenium oxide is preferred in a further embodiment. Particularly preferred is a salt of $SeO_2$, e.g. $Na_2SeO_3$.

Furthermore, the above-mentioned kit may contain a cytostatic which is a mitosis-inhibiting cytostatic, e.g. selected from the above-mentioned compounds. Furthermore, the cytostatic may also be a cytostatic inhibiting nucleic acid synthesis. The compounds gemcitabine and mitomycin C are here particularly preferred cytostatics inhibiting nucleic acid synthesis.

The kit according to the invention contains selenium and/or at least one selenium compound in a concentration of 0.1 mg/kg body weight to 1.25 mg/kg body weight and a cytostatic as described above in a concentration of 2 mg/$M^2$ body surface to 240 mg/$M^2$ body surface. A concentration range of 0.1 mg/kg body weight to 0.3 mg/kg body weight is here preferred for selenium or a selenium compound, and a concentration range of 20 mg/kg body weight to 1000 mg/$M^2$ body weight of a cytostatic as characterized above.

The combinations of a selenium compound and a cytostatic or several cytostatics can be administered in solid or liquid form. The application may be oral, rectal, nasal, topical (including buccal and sublingual), vaginal or parenteral (including intramuscular, subcutaneous and intravenous), or by inhalation. They may be administered together with conventional adjuvants, carriers and/or diluents.

The solid forms of application comprise tablets, capsules, powders, pills, pastilles, suppositories and granular forms of administration. They may also include additives, such as flavors, dyes, diluents, softeners, binders, preservatives, blasting agents and/or enclosing materials.

Liquid forms of administration include solutions, suspensions and emulsions. These may also be offered together with the above-mentioned additives.

The following figures and examples will explain the present invention:

FIG. 1: Effect of sodium selenite (3 $\mu$M and 30 $\mu$M) on the colony formation of pancreatic tumor xenografts (PAXF 546 and 736) in the clonogenic assay in vitro in different experiments. T/C=number of tumor colonies in the selenium-treated samples divided by number of colonies in the untreated samples in %.

Figure 2:
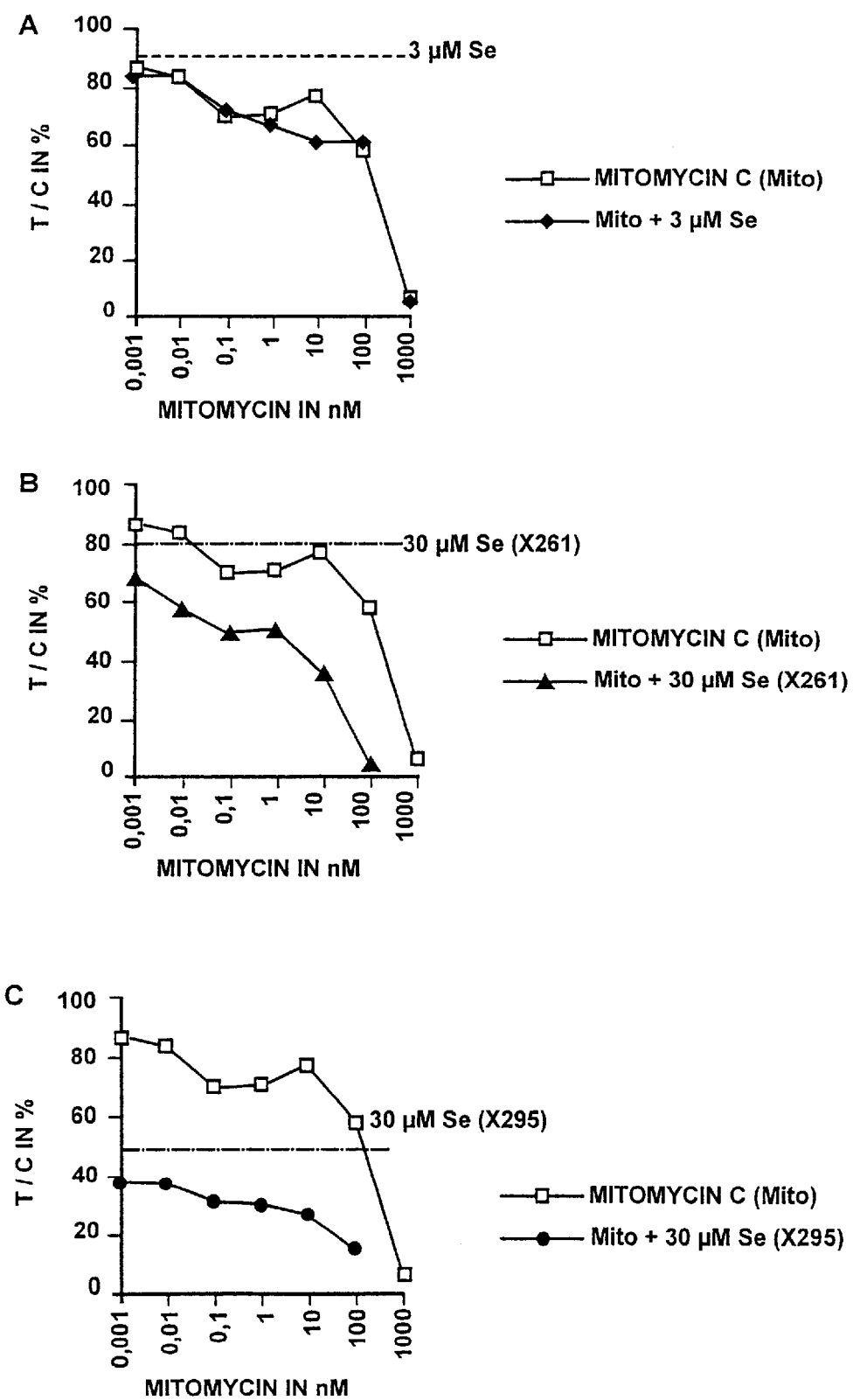

FIG. 2: Effect of selenium and mitomycin C given alone or simultaneously on the in vitro growth of the pancreatic tumor xenograft PAXF 546 (clonogenic assay, continuous drug exposure). A–C: Dose/response curves of mitomycin C und mytomycin C in combination mit 3 $\mu$M selenium (A) or 30 $\mu$M selenium (B, C). The effect of selenium alone is indicated by the dashed lines.

Figure 3:
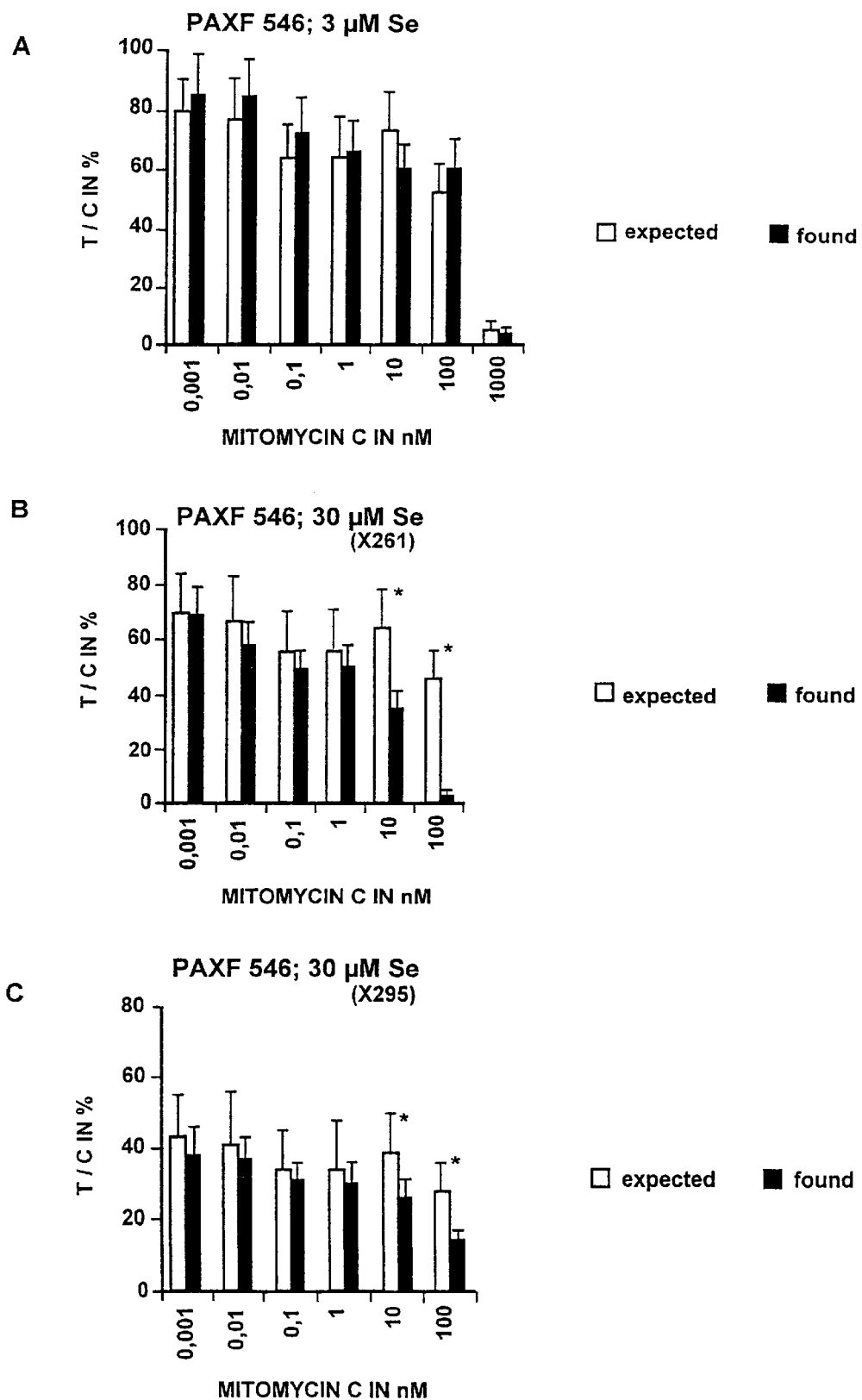

FIG. 3: Comparison of the experimentally observed and expected T/C values for seleniumlmitomycin C combinations. Expected T/C values for an additive drug effect are shown as open bars, experimentally observed T/C values as solid bars;

indicates a significant difference (p<0,01) between $T/C_{expected}$ and $T/C_{observed}$ and therefore drug synergism. A–C: Combination of mitomycin C with 3 $\mu$M selenium (A) or 30 $\mu$M selenium (B, C).

Figure 4:
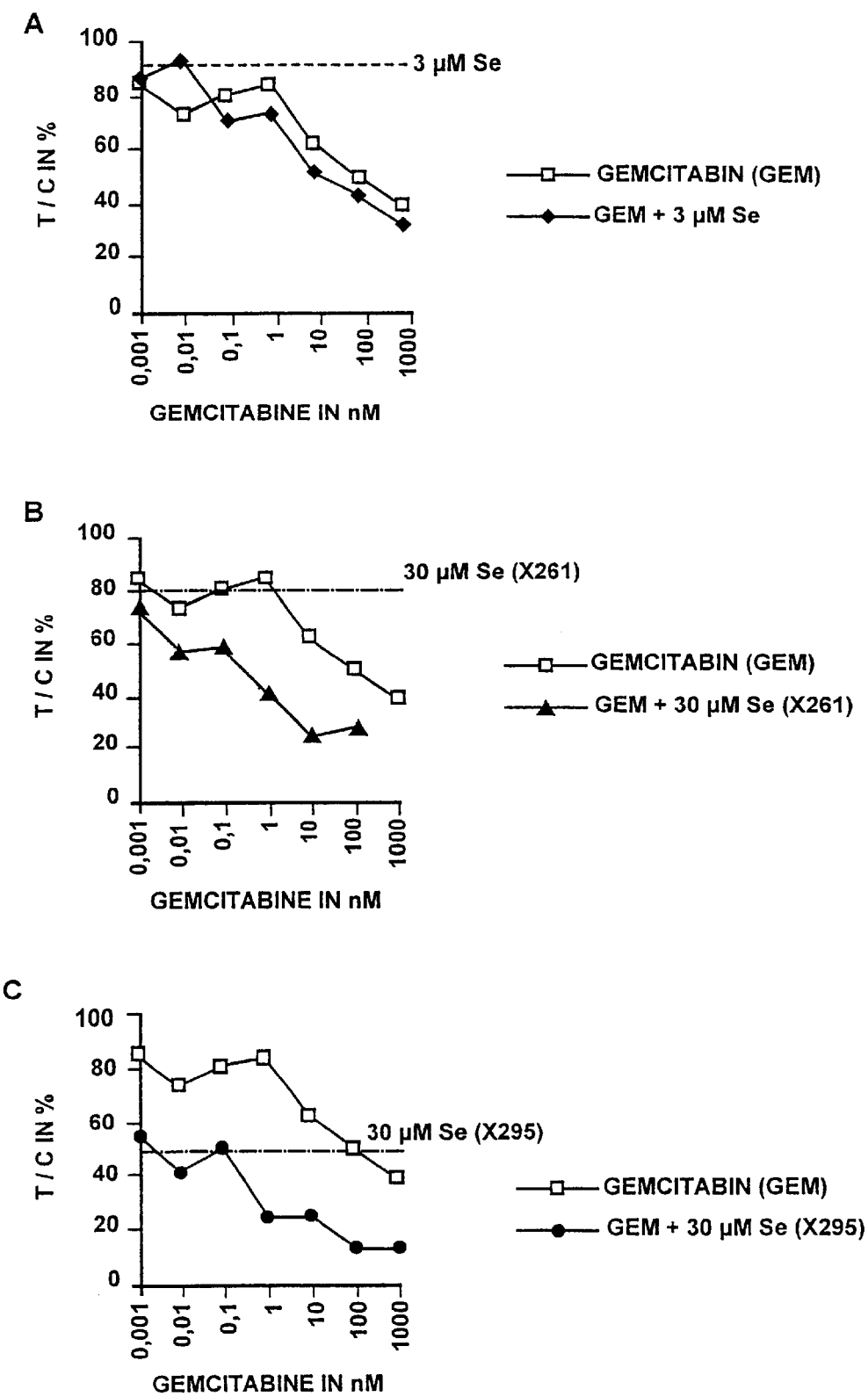

FIG. 4: Effect of selenium gemcitabine given alone or in combination on the in vitro growth of the pancreatic tumor xenograft PAXF 546 (clonogenic assay, continuous drug exposure). A–C: Dose/response curve of gemcitabine alone and gemcitabine in combination with 3 $\mu$M selenium (A) or 30 $\mu$M selenium (B, C). The effect of selenium alone is indicated by the dashed lines.

FIG. 5: Comparison of the experimentally observed and expected T/C values of selenium/gemcitabine combinations. Expected T/C values for the additive drug effect are shown as open bars, experimentally observed T/C values as solid bars;

indicates a significant difference (p<0,01) between $T/C_{expected}$ and $T/C_{observed}$ and therefore drug synergism. A–C: Combination of gemcitabine with 3 $\mu$M selenium (A) or 30 $\mu$M selenium (B, C).

EXAMPLES

1. Material and Methods

Sodium selenite (Selenase®) was provided by G. N. Pharm GmbH, Fellbach, Germany. The 0.9% NaCl solution contained 50 $\mu$g/ml (0,63 mM) of selenium as $Na_2SeO_3 \times 5H_2O$. Gemcitabine and mitomycin C were purchased from the pharmacy and used as clinical formulations.

1.1 Colony Forming Assay

Preparation of a Single Cell Suspension From Human Tumor Xenografts

Solid human tumor xenografts growing subcutaneously in serial passages in thymus-aplastic nude mice (NMRI nu/nu strain, obtained from our own breeding facility) were removed under sterile conditions, the cells were mechanically disaggregated and subsequently incubated with an enzyme cocktail consisting of collagenase (1.2–1.8 U/ml, Worthington), DNAse (375 U/ml, Boehringer Mannheim) und hyaluronidase (29 U/ml, Boehringer Mannheim) in RPMI 1640 at 37° C. for 30 minutes. The cell mixture was passed through sieves of 200 $\mu$m and 50 $\mu$m mesh size and washed thereafter twice with PBS. The percentage of viable cells was determined in a Neubauer counting chamber using trypan blue exclusion.

1.2 Culture Methods

The clonogenic assay was performed according to a modified two-layer soft agar assay described by Hamburger and Salmon (Hamburger and Salmon, Science, 197: 461463, 1977). The bottom layer consisted of 0.2 ml Iscoves' Modified Dulbecco's Medium with 20% fetal calf serum and 0.75% agar. $8 \times 10^3$ to $1,6 \times 10^4$ cells were added to 0.2 ml of the same culture medium together with 0.4% agar and placed in already coated 24-multiwell dishes. Test substances were applied by continuous exposure (drug overlay) in 0.2 ml medium. Every dish included six control wells containing the vehicle- and drug-treated groups in triplicate at six concentrations.

Cultures were incubated at 37° and 7% $CO_2$ in a humidified atmosphere for 5 to 15 days (depending on the doubling time of the tumor stem cells) and monitored for colony growth using an inverted microscope. Within this period, in vitro tumor growth led to the formation of colonies with a diameter of $\geq 50$ μm. At the time of maximum colony formation counts were performed with an automatic image analysis system (OMNICOM Fas IV, Biosys GmbH). 24 hours prior to this assay, vital colonies were stained with a sterile aqueous solution of 2-(4-iodophenyl)-3-(4-nitrophenyl)-5-phenyltetrazolium chloride (1 mg/ml, 100 μl/well). Drug effects were expressed in terms of the percentage of surviving cells, obtained by comparison of the mean number of colonies in the treated plates with the mean colony count of the untreated controls (test-versus-control-group value, T/C=colony count$_{Treated\ Group}$*100/colony count$_{Control\ Group}$).

An assay was considered as significant if the following quality control criteria were fulfilled:

Mean number of colonies in the control group dishes for 24-multiwells $\geq 20$ colonies with a colony diameter of $\geq 50$ μm.

Colony survival number in wells treated with the positive reference compound 5-fluorouracil (at the toxic dose of 1000 μg/ml) <30% of the controls.

Coefficient of variation in the control group $\leq 50\%$. $IC_{50}$ and $IC_{70}$ values were determined by plotting compound concentration versus cell survival rate. Mean $IC_{50}$ and $IC_{70}$ values were calculated according to the formula:

$$\text{mean}\ IC_{50}\ \text{and}\ IC_{70} = \frac{\sum_{x=1}^{n} \log(IC_{50,70})_x}{n}$$

with x=specific tumor xenograft and n=total number of tumor xenografts studied. If an $IC_{50}$ or $IC_{70}$ value could not be determined within the examined dose range, the lowest or highest concentration studied was used for the calculation.

1.3 Combination Studies

The inhibition of colony formation by the chemotherapeutic agents gemcitabine and mitomycin C alone as well as in combination with selenium was studied in pancreatic human tumor xenografts PAXF 546 and 736 applying the clonogenic assay as described above. Each experiment included the chemotherapeutic agents in 6 concentrations, selenium in 2 concentrations (3 and 30 μM), and the combination of all doses with selenium at 3 and 30 μM. All compounds and combinations were studied in triplicates. Concentrations of the chemotherapeutic agents were chosen in such a way that T/C values of 0 to 100% resulted therefrom. Each experiment was performed twice. The effect of a combination of compounds was determined by comparing the experimentally observed T/C value of a selenium/cytostatic combination (T/C$_{observed}$(A+B)) with the expected T/C value for this combination (T/C$_{expected}$(A+B)), calculated by multiplying the number of surviving colonies obtained after treatment of the cells with the respective individual substances (T/C (A) und T/C (B)) using the following equation (multiplication method, for example described by Berenbaum, 1989, Pharmacol. Rev., 41:93–141):

$$T/C_{expectd}(A+B)=T/C(A)\times T/C(B)/100$$

For a zero-interactive drug combination (additivity of drug effects) T/C$_{expected}$(A+B)×T/C$_{observed}$(A+B). A drug combination is synergistic if T/C$_{observed}$(A+B) is statistically significant>T/C$_{expected}$(A+B). Statistical significance was determined by the T-test.

2. Results 2.1. In Vitro Antitumor Activity of Sodium Selenite in Human Tumor Xenografts The cytotoxic activity of sodium selenite was studied on the following human tumor xenografts using the clonogenic assay:

TABLE 1

Human tumor xenografts examined

| Tumor | | Original Histology |
|---|---|---|
| Lung | LXFL 529 | non small cell bronchial carcinoma |
| | LXFS 650 | small cell bronchial carcinoma |
| Breast | MAXF 401NL | adenocarcinoma, estrogen receptor negative, progesterone receptor negative |
| | MAXF MCF7X | adenocarcinoma, estrogen receptor negative, progesterone receptor negative |
| Ovary | OVXF 899 | adenocarcinoma |
| | OVXF 1353 | adenoid carcinoma |
| Pancreas | PAXF 546 | adenosquamous carcinoma |
| | PAXF 736 | adenocarcinoma |
| Prostate | PC3MX | adenocarcinoma |
| | DU145X | carcinoma |
| Kidney | RXF 393 | hypernephroma |
| | RXF 944LX | hypernephroma |

Sodium selenite concentrations between 0.001 and 100 μM were applied. T/C values obtained in the various tumor xenografts are shown in Table 2. $IC_{50}$ and $IC_{70}$ values as well as an $IC_{70}$ bar diagram, which shows the sensitivity of the various tumors to selenium treatment, are given in Table 3.

Inhibition of the colon formation depends on the selenium dose. With amounts up to 1 μM no distinct cytotoxic effect could be observed. At 10 μM selenium T/C values between 30% were obtained in 2 of 12 xenografts (LXFL 529, PRXF DU145X). At very high selenium concentrations of 100 μM, T/C values below 20% were obtained in all xenografts, which points at an unspecific cytotoxic effect.

TABLE 2

In vitro effect of sodium selenite in human tumor xenografts

| TUMOR/PASSAGE No. | EXP. No. | Test/control (%) at drug concentration [$\mu$M] | | | | | |
|---|---|---|---|---|---|---|---|
| | | .001 | .01 | .1 | 1. | 10. | 100. |
| LXFL | | | | | | | |
| 529/18 | X182AM | 90− | 78− | 72− | 61− | 9+++ | 0+++ |
| LXFS | | | | | | | |
| 650/9 | X199AM | 100− | 100− | 98− | 84− | 109− | 16++ |
| MAXF | | | | | | | |
| 401/16 | X186AM | 67s− | 81s− | 53− | 74− | 66− | 8+++ |
| MCF7X/28 | X218AM | 93− | 85− | 90− | 78− | 97− | 0+++ |
| OVXF | | | | | | | |
| 899/33 | X185AM | 80− | 79− | 66− | 70− | 73− | 1+++ |
| 1353/17 | X217AM | 96− | 91− | 100− | 90− | 100− | 0+++ |
| PAXF | | | | | | | |
| 546/2 | *(2) | 82− | 112− | 100− | 104− | 88− | 2+++ |
| 736/17 | X184AM | 87− | 77− | 94− | 88− | 90− | 4+++ |
| PRXF | | | | | | | |
| PC3M/3 | X189/AM | 91− | 91− | 89− | 85− | 38+ | 1+++ |
| DU145X/15 | X229AM | 97− | 96− | 92− | 91− | 5+++ | 0+++ |
| RXF | | | | | | | |
| 393/9 | X194AM | 62− | 45− | 31+ | 31+ | 32+ | 10+++ |
| 423/16 | X183AM | 99− | 111− | 120− | 92− | 110− | 0+++ |
| active(++, +++)/total | | 0/12 | 0/12 | 0/12 | 0/12 | 2/12 | 12/12 |
| xenografts only | | 0% | 0% | 0% | 0% | 17% | 100% |

Table legend:
LXF lungs, A adeno, L large cell, S small cell cancer xenograft;
MAXF breast cancer xenograft;
OVXF ovary cancer xenograft,
PAXF pancreas,
PRXF prostate cancer xenograft;
RXF kidney cancer xenograft
− (T/C ≧ 50%);
+ (30% ≦ T/C < 50%);
++ (10% < T/C < 30%);
+++ (T/C ≦ 10%),
s result of a dish In the $IC_{70}$ bar diagram ($IC_{70}$ plot, Table 3) variations of individual $IC_{70}$ values from the mean value are expressed as bars in the logarithmic representation. Bars to the left demonstrate $IC_{70}$ values lower than the mean value, bars to the right demonstrate higher values. The $IC_{70}$ plot represents therefore a characteristic antiproliferative profile of the compound.

The mean $IC_{50}$ of sodium selenite was 15.5 $\mu$M, the mean $IC_{70}$ value 27 $\mu$M. This corresponds to a selenium concentration of 1,2 $\mu$g/ml (mean $IC_{50}$) and 2.1 $\mu$g/ml (mean $IC_{70}$).

Compared with the efficiency of standard chemotherapeutic agents in this assay, the values are within the scope of the $IC_{50}$ and $IC_{70}$ values of the alkylating agents ifosfamide and cyclophosphamide. Most of the other standard alkylating agents have mean $IC_{70}$ values of <0,1 $\mu$g/ml.

The most sensitive tumor xenografts, represented by $IC_{70}$ values and bars to the left in Table 3, were the large lung cell cancer xenograft LXFL 529, the kidney cancer xenograft RXF 393 and the prostate xenograft PC3M and DU145X.

TABLE 3

In vitro effect of sodium selenite in human tumor xenografts

| TUMOR/PASSAGE No. | Colony contr. | Distribution of $IC_{70}$ related to mean log scaled axis | $IC_{50}$ μm | $IC_{70}$ μm |
|---|---|---|---|---|
| LXFL 529/18 | 129 | | 1.627 | 3.945 |
| LXFS 650/9 | 107 | | 43.093 | 70.706 |
| MAXF 401/16 | 37 | | 18.873 | 41.753 |
| MCF7X/28 | 200 | | 30.516 | 49.059 |
| OVXF 899/33 | 50 | | 20.866 | 39.556 |
| 1353/17 | 120 | | 31.622 | 50.118 |
| PAXF 546/2 | 80 | | 27.660 | 47.251 |
| 736/17 | 55 | | 29.182 | 49.851 |
| PRXF PC3M/3 | 140 | | 5.554 | 16.451 |
| OU145X/1 | 254 | | 2.997 | 5.120 |
| RXF 393/9 | 23 | | n.e. | 12.328 |
| 423/16 | 97 | | 35.111 | 53.366 |
| Mean | n = 12 | 26.967 | 15.5 | 27.0 |

2.2 In Vitro Combination Studies

To examine whether selenium given as sodium selenite can potentiate the antiproliferative effect of standard chemotherapeutic agents, two pancreatic human tumor xenografts (PAXF 546 und PAXF 736) were exposed to gemcitabine, mitomycin C or sodium selenite alone or to sodium selenite combined with one of the two chemotherapeutic agents.

Fixed concentrations of sodium selenite (3 or 30 μM) were administered to the cells together with 6 different concentrations of the chemotherapeutic agents. According to the data shown in Table 2, a sodium selenite concentration of 3 μM was expected to influence colony formation of the two pancreatic tumors only marginally. This was confirmed by the results when sodium selenite was used as a single agent at this concentration in the combination studies (FIG. 1). The higher sodium selenite concentrations of 30 μM should have a stronger influence on tumor colony formation, since the tumor colony formation rate of both pancreactic tumors rapidly decreases when the sodium selenite concentration increases from 10 to 100 μM (Table 2). This could be proven in the further experiments in FIG. 1. The variation of T/C values at 30 μM in the two experiments (FIG. 1) is caused by the very steep dose/response values of sodium selenite at concentrations around 30 μM. Therefore, combination experiments with PAXF 546 at this selenium concentration were evaluated separately. In the case of PAXF 736 only experiment X265 could be used for evaluation since in experiment X290 30 μM of selenium were already strongly cytotoxic with a T/C value of 5%.

The following Tables 4a to 4d show the results of incubation of two pancreatic xenografts with different concentrations of selenium and the cytostatics mitomycin C and gemcitabine. To determine whether a drug combination has an additive effect of the individual drugs, the experimentally determined T/C values for a specific combination were compared with the values expected for an additive effect (see Materials and Methods). When the pancreatic tumor xenograft PAXF 736 was treated simultaneously with sodium selenite and mitomycin C or gemcitabine, no synergistic effect could be detected, neither at a concentration of 3 μM nor at a concentration of 30 μM sodium selenite. Also no synergism was observed between 3 μM sodium selenite and all of the tested concentrations of chemotherapeutic agents in the xenograft PAXF 546 or when low concentrations of the chemotherapeutic agents were combined with 30 μM of sodium selenite. In contrast, when higher doses of chemotherapeutic drugs at which cytotoxic effects could be observed were combined with 30 μM sodium selenite, synergism was observed in combination with mitomycin C and gemcitabine (Tables 4a, 4b).

TABLE 4a

Inhibition of colony growth of the pancreatic cancer xenograft PAXF 546 by $Na_2SeO_3$ or mitomycin C alone or in combination in vitro

| Treatment | | Sodium selenite Conc. in μM | T/C in % | T/C in % at a mitomycin C concentration (μM) of | | | | | | | Synergism |
|---|---|---|---|---|---|---|---|---|---|---|---|
| | | | | $1 \times 10^{-6}$ | $1 \times 10^{-5}$ | $1 \times 10^{-4}$ | $1 \times 10^{-3}$ | $1 \times 10^{-2}$ | $1 \times 10^{-1}$ | 1.0 | |
| Mitomycin C | (X261, X295) | | | 87 ± 11 | 84 ± 14 | 70 ± 10 | 70 ± 13 | 80± 12 | 57 ± 8 | 5 ± 2 | |
| Mitomycin C + 3 μM Se | expect. obs.* (X261, X295) | 3.0 | 91 ± 8 | 84 ± 15 | 84 ± 13 | 72 ± 12 | 66 ± 10 | 60 ± 8 | 60 ± 10 | 4 ± 2 | no |
| | expect.** | | | 76 ± 12 | 76 ± 15 | 64 ± 11 | 64 ± 14 | 73 ± 13 | 52 ± 9 | 5 ± 3 | |
| Mitomycin C + 30 μM Se | expect. obs. (X261) | 30.0 | 80 ± 13 | 69 ± 10 | 58 ± 8 | 49 ± 7 | 50 ± 8 | 35 ± 6*** | 3 ± 2 | | partial |
| | expected | | | 70 ± 14 | 67 ± 16 | 56 ± 14 | 56 ± 15 | 64 ± 14 | 46 ± 10 | | |
| | expect. obs. (X295) | 30.0 | 49 ± 6 | 38 ± 8 | 37 ± 6 | 31 ± 5 | 30 ± 6 | 26 ± 5 | 14 ± 3 | | partial |
| | expected | | | 43 ± 12 | 41 ± 15 | 34 ± 11 | 34 ± 14 | 39 ± 12 | 28 ± 9 | | |

*experimentally observed T/C values for the combination of mitomycin C and selenium
**expected T/C values for the combination, calculated by the method: $T/C_{expected} = T/C_{se} \times T/C_{drug}/100$; T/C:T/C value in % with a given treatment at a given concentration
***synergistic drug concentrations are marked in italics.

TABLE 4b

Inhibition of colony growth of the pancreatic cancer xenograft PAXF 546 by $Na_2SeO_3$ or gemcitabine alone or in combination in vitro

| Treatment | | Sodium selenite Conc. in μM | T/C in % | T/C in % at a gemcitabine concentration (μM) of | | | | | | | Synergism |
|---|---|---|---|---|---|---|---|---|---|---|---|
| | | | | $1 \times 10^{-6}$ | $1 \times 10^{-5}$ | $1 \times 10^{-4}$ | $1 \times 10^{-3}$ | $1 \times 10^{-2}$ | $1 \times 10^{-1}$ | 1.0 | |
| Gemcitabine | (X261, X295) | | | 85 ± 15 | 73 ± 20 | 80 ± 12 | 83 ± 12 | 61± 11 | 48 ± 8 | 30 ± 6 | |
| Gemcitabine + 3 μM Se | expect. obs.* (X261, X295) | 3.0 | 91 ± 8 | 86 ± 16 | 93 ± 16 | 70 ± 18 | 72 ± 11 | 50 ± 9 | 41 ± 10 | 30 ± 10 | no |
| | expect.** | | | 77 ± 17 | 66 ± 23 | 73 ± 14 | 76 ± 14 | 56 ± 12 | 44 ± 10 | 34 ± 8 | |
| Gemcitabine + 30 μM Se | expect. obs. (X261) | 30.0 | 80 ± 13 | 74 ± 12 | 57 ± 7 | 58 ± 7 | 40 ± 8*** | 24 ± 7 | 27 ± 4 | | partial |
| | expected | | | 68 ± 17 | 58 ± 23 | 64 ± 15 | 66 ± 15 | 49 ± 14 | 38 ± 12 | | |
| | expect. obs. (X295) | 30.0 | 49 ± 6 | 55 ± 12 | 41 ± 10 | 50 ± 9 | 23 ± 7 | 23 ± 6 | 11 ± 6 | 10 ± 3 | partial |
| | expected | | | 43 ± 14 | 36 ± 21 | 39 ± 13 | 41 ± 13 | 30 ± 12 | 24 ± 9 | 18 ± 7 | |

*experimentally observed T/C values for the combination of gemcitabine and selenium
**expected T/C values for the combination, calculated by the method: $T/C_{expected} = T/C_{se} \times T/C_{drug}/100$; T/C:T/C value in % with a given treatment at a specific concentration
***synergistic drug concentrations are marked in italics.

TABLE 4c

Inhibition of colony growth of the pancreatic cancer xenograft PAXF 736 by $Na_2SeO_3$ or mitomycin C alone or in combination in vitro

| Treatment | | Sodium selenite Conc. in μM | T/C in % | T/C in % at a mitomycin C concentration (μM) of | | | | | | Synergism |
|---|---|---|---|---|---|---|---|---|---|---|
| | | | | $1 \times 10^{-6}$ | $1 \times 10^{-5}$ | $1 \times 10^{-4}$ | $1 \times 10^{-3}$ | $1 \times 10^{-2}$ | $1 \times 10^{-1}$ | |
| Mitomycin C | (X261, X295) | | | 77 ± 13 | 58 ± 10 | 56 ± 11 | 46 ± 8 | 30± 7 | 11 ± 7 | |
| Mitomycin C + 3 μM Se | expect. obs.* (X265, X290) | 3.0 | 81 ± 12 | 90 ± 15 | 60 ± 11 | 56 ± 8 | 48 ± 7 | 29 ± 3 | 10 ± 3 | no |
| | expect.** | | | 70 ± 16 | 53 ± 13 | 51 ± 13 | 42 ± 12 | 27 ± 9 | 10 ± 9 | |

TABLE 4c-continued

Inhibition of colony growth of the pancreatic cancer xenograft PAXF 736 by $Na_2SeO_3$ or mitomycin C alone or in combination in vitro

| Treatment | | Sodium selenite Conc. in $\mu M$ | T/C in % | T/C in % at a mitomycin C concentration ($\mu M$) of | | | | | | Synergism |
|---|---|---|---|---|---|---|---|---|---|---|
| | | | | $1 \times 10^{6}$ | $1 \times 10^{-5}$ | $1 \times 10^{-4}$ | $1 \times 10^{-3}$ | $1 \times 10^{-2}$ | $1 \times 10^{-1}$ | |
| Mitomycin C + 30 $\mu M$ Se | expect. obs. (X265) | 30.0 | 43 ± 8 | 25 ± 10 | 15 ± 7 | 27 ± 7 | 17 ± 6 | 19 ± 6 | 4 ± 3 | no |
| | expected | | | 33 ± 14 | 25 ± 11 | 24 ± 12 | 20 ± 9 | 14 ± 8 | 5 ± 5 | |
| | expect. obs. (X290) | 30.0 | 5 ± 2 | 4 ± 2 | 3 ± 2 | 3 ± 3 | 2 ± 2 | 1 ± 1 | 1 ± 1 | n.d.*** |
| | expected | | | | | | | | | |

*experimentally observed T/C values for the combination of mitomycin C and selenium
**expected T/C values for the combination, calculated by the multiplication method: $T/C_{expected} = T/C_{se} \times T/C_{drug}/100$; T/C:T/C value in % with a given treatment at a specific concentration
***not determined TABLE 4d Inhibition of colony growth of the pancreatic cancer xenograft PAXF 736 by $Na_2SeO_3$ or gemcitabine alone or in combination in vitro

| Treatment | | Sodium selenite Conc. in $\mu M$ | T/C in % | T/C in % at a gemcitabine concentration ($\mu M$) of | | | | | | Synergism |
|---|---|---|---|---|---|---|---|---|---|---|
| | | | | $1 \times 10^{6}$ | $1 \times 10^{-5}$ | $1 \times 10^{-4}$ | $1 \times 10^{-3}$ | $1 \times 10^{-2}$ | $1 \times 10^{-1}$ | |
| Gemcitabine | (X261, X295) | | | 89 ± 11 | 78 ± 14 | 84 ± 12 | 77 ± 13 | 71 ± 10 | 30 ± 8 | |
| Gemcitabine + 3 $\mu M$ Se | expect. obs.* (X265, X290) | 3.0 | 81 ± 12 | 79 ± 13 | 82 ± 12 | 84 ± 12 | 86 ± 15 | 66 ± 10 | 18 ± 8 | no |
| | expect.** | | | 72 ± 12 | 63 ± 16 | 68 ± 13 | 62 ± 14 | 58 ± 12 | 24 ± 9 | |
| Gemcitabine + 30 $\mu M$ Se | expect. obs. (X265) | 30.0 | 43 ± 8 | 64 ± 15 | 62 ± 20 | 59 ± 13 | 39 ± 7 | 34 ± 6 | 14 ± 5 | no |
| | expected | | | 38 ± 12 | 34 ± 15 | 36 ± 13 | 33 ± 14 | 31 ± 11 | 13 ± 9 | |
| | expect. obs. (X290) | 30.0 | 5 ± 2 | 9 ± 7 | 5 ± 3 | 4 ± 3 | 5 ± 3 | 3 ± 2 | 1 ± 1 | n.d.*** |
| | expected | | | | | | | | | |

*experimentally observed T/C values for the combination of gemcitabine and selenium
**expected T/C values for the combination, calculated by the multiplication method: $T/C_{expected} = T/C_{se} \times T/C_{drug}/100$; T/C:T/C value in % with a given treatment at a specific concentration
***not determined TABLE 5a Synergistic effects of selenium in combination with gemcitabine in vitro

| Xeno-graft | Exp. no. | Se conc. [$\mu M$] | Synergism with gemcitabine [$\mu m$] | | | | | | |
|---|---|---|---|---|---|---|---|---|---|
| | | | $1 \times 10^{-6}$ | $1 \times 10^{-5}$ | $1 \times 10^{-4}$ | $1 \times 10^{-3}$ | $1 \times 10^{-2}$ | 0.1 | 1.0 |
| PAXF 546 | X251, X295 | 3.0 | –* | – | – | – | – | – | – |
| | X261 | 30.0 | – | – | – | +* | + | + | n.d. |
| | X295 | 30.0 | – | – | – | + | + | + | + |
| PAXF 736 | X265, X290 | 3.0 | – | – | – | – | – | – | n.d. |
| | X265 | 30.0 | – | – | – | – | – | – | n.d. |
| | X290 | 30.0 | | | | not evaluable | | | |

TABLE 5b

Synergistic effects of selenium in combination with mitomycin C in vitro

| Xenograft | Exp. no. | Se conc. [μM] | Synergism with mitomycin C [μm] | | | | | | |
|---|---|---|---|---|---|---|---|---|---|
| | | | $1 \times 10^{-6}$ | $1 \times 10^{-5}$ | $1 \times 10^{-4}$ | $1 \times 10^{-3}$ | $1 \times 10^{-2}$ | 0.1 | 1.0 |
| PAXF 546 | X251, X295 | 3.0 | −* | − | − | − | − | − | − |
| | X261 | 30.0 | − | − | − | − | +* | + | n.d. |
| | X295 | 30.0 | − | − | − | − | + | + | + |
| PAXF 736 | X265, X290 | 3.0 | − | − | − | − | − | − | n.d. |
| | X265 | 30.0 | − | − | − | − | − | − | n.d. |
| | X290 | 30.0 | | | not evaluable | | | | |

*The experimentally determined T/C value for a drug combination is markedly lower (+) or not lower (−) than the expected T/C value for this combination:
n.d.: not determined.

In FIGS. 2 and 3 the effect of sodium selenite and mitomycin C is demonstrated on the in vitro growth of PAXF 546. When 3 μM sodium selenite were added to different concentrations of mitomycin C, no change in the dose/response curve of mitomycin C could be observed, and therefore no synergism between the two drugs occurs at this low concentration of selenite (FIGS. 2a and 3a).

However, when 30 μM of sodium selenite were given simultaneously with mitomycin C, synergism was found at mitomycin C concentrations>0.01 μM (FIGS. 2b, c, 3b, c and Table 5b).

Similar results were obtained with the combination of sodium selenite and gemcitabine (FIGS. 4 and 5, Table 5a). Synergistic inhibition of colony formation in PAXF 546 was only found at a selenium concentration of 30 μM and a gemcitabine concentration higher than 0.1 nM (FIG. 5, Table 5a).

In summary, the results show that high doses of selenium reduce the growth of many human tumor xenografts in vitro. Simultaneous treatment of the pancreatic cancer cells PAXF 546 with 30 μM selenium and cytostatics, which directly react with the cellular DNA (e.g. gemcitabine and mitomycin C), results in a synergistic inhibition of the tumor growth in vitro.

3. Case Studies

The case documentations of five male tumor patients who received a combination therapy of highly dosed selenium (10–30 mg) and various cytostatics are listed in the following. Two of the patients with pancreatic carcinoma (patient no. 4, 5) responded well to the therapy despite highly advanced diseases, also two patients (patient no. 1, 3) with hormone-resistant metastasized prostatic carcinoma. One patient (patient no. 2) with metastasized hypemephroma reacted with a partial remission to the therapy.

Patient No. 1

1.) Diagnosis: hormone-resistant metastasized prostatic carcinoma
2.) Diagnosed (month/year): June 1994
3.) Histology: cribriform prostatic carcinoma, degree III
4.) Tumor stage at the beginning of the therapy: T3, N2, M1
   (T=extension of the primary tumor N=presence of lymph node metastases M=presence of distant metastases)
5.) Localization of the distant metastases: lymph nodes, bones
6.) Tumor pretreatment: hormone therapy from VI/94 to XI/94
7.) Therapy with chemotherapy/selenium:
   a) Chemotherapeutic agent: 5-fluorouracil, 750 mg, i.v., from XI/94 to V/95 mitomycin, 10 mg, i.v., from XI/94 to V/95
   b) Selenium: Selenase®, 10 mg, i.v., from XI/94 to V/95
   c) Response to the therapy: partial remission, complete regression of lymphatic edemata
   d) Duration of the response: 7 months
   e) Reason for terminating the therapy: progression
   f) Therapy tolerance: good
8.) Preceding and concomitant diseases: coronary heart disease since 1991, still existing at the beginning of the therapy
9.) Accompanying therapy during chemo/selenium therapy: Kerlone, Adalat from 1991 to V/95
10.) Survival status: dead
   date of death: Aug. 31, 1994; due to tumor Patient No. 2

1.) Diagnosis: metastasized hypemephroma
2.) Diagnosed (month/year): April 1996
3.) Histology: hypernephroma
4.) Tumor stage at the beginning of the therapy: T2, N1, M1
   (T=extension of the primary tumor N=presence of lymph node metastases M=presence of distant metastases)
5.) Localization of distant metastases: lung, liver
6.) Tumor pretreatment: nephrectomia 1996; interleukin II from IX/97 to I/98
7.) Therapy with chemotherapy/selenium:
   a) Chemotherapeutic agent: Gemzar, 2 g, i.v., from I/98 to V/98
   b) Selenium: Selenase®, 30 mg, i.v. from I/98 to V/98
   c) Response to the therapy: partial remission
   d) Duration of the response: so far 5 months
   e) Reason for terminating the therapy: none
   f) Therapy tolerance: good
8.) Preceding and concomitant diseases: polycythemia since 1990; still existing at the beginning of the therapy
9.) Accompanying therapy during chemo/selenium therapy: none
10.) Survival status: living; last observed May 18, 1998

Patient No. 3

1.) Diagnosis: metastasized hormone-resistant prostatic carcinoma

2.) Diagnosed (month/year): May 1997
3.) Histology: adenocarcinoma, degree II
4.) Tumor stage at the beginning of the therapy: T3, N1, M1
   (T=extension of the primary tumor N=presence of lymph node metastases M=presence of distant metastases)
5.) Localization of the distant metastases: bones
6.) Tumor pretreatment: orchiectomy at both sides 1997
7.) Therapy with chemotherapy/selenium:
   a) Chemotherapeutic agent: adriblastine, 40 mg, i.v., from II/98 to V/98
   b) Selenium: Selenase®, 30 mg, i.v., from II/98 to V/98
   c) Response of the therapy: total remission
   d) Duration of the response: so far 3 months
   e) Reason for terminating the therapy: none
   f) Therapy tolerance: good
8.) Preceding and concomitant diseases: none
9.) Accompanying therapy during chemo/selenium therapy: bisphosphonate (Bondronat) from II/98 to V/98
10.) Survival status: living, last observed May 20, 1998

Patient No. 4
1.) Diagnosis: pancreatic carcinoma
2.) Diagnosed (month/year): October 1994
3.) Histology: adenocarcinoma, degree II
4.) Tumor stage at the beginning of the therapy: T4, N1, M0
   (T=extension of the primary tumor N=presence of lymph node metastases M=presence of distant metastases)
5.) Localization of the distant metastases: none
6.) Tumor pretreatment: explorative laparotomy 1994, gastroenterostomy
7.) Therapy with chemotherapy/selenium:
   a) Chemotherapeutic agent: 5-fluorouracil, 750 mg, i.v., from X/94 to VI/95, mitomycin, 10 mg, i.v., from X/94 to VI/95
   b) Selenium: Selenase® 10 mg, i.v., from X/94 to VI/95
   c) Response to the therapy: total remission, freedom from pain, weight gain
   d) Duration of the response: 9 months
   e) Reason for terminating the therapy: VI/95 cerebral metastasis
   f) Therapy tolerance: good
8.) Preceding and concomitant diseases: none
9.) Accompanying therapy during chemo/selenium therapy: none
10.) Survival status: date of death Aug. 29, 1995; due to tumor Patient No. 5
1.) Diagnosis: pancreatic carcinoma and gastric carcinoma
2.) Diagnosed (month/year): November 1997
3.) Histology: adenocarcinoma, degree III
4.) Tumor stage at the beginning of the therapy: T4, N1, M1
   (T=extension of the primary tumor N=presence of lymph node metastases M=presence of distant metastases)
5.) Localization of the distant metastases: liver, lymph nodes
6.) Tumor pretreatment:
   a) Surgery: explorative laparotomy, gastroenterostomy 1997
   b) Chemotherapy: Gemzar from XI/97 to I/98, high-dose 5-fluorouracil and leucovorins from I/98 to III/98, oxaliplatin from III/98 to IV/98
7.) Therapy with chemotherapy/selenium:
   a) Chemotherapeutic agent: Gemzar, 1,2 mg, i.v., from IV/98 to V/98 mitomycin, 10 mg, i.v. from IV/98 to V/98
   b) Selenium: Selenase®, 30 mg, i.v., from IV/98 to V/98
   c) Response to the therapy: partial remission, substantial pain reduction
   d) Duration of the response: 1 month
   e) Reason for terminating the therapy: death
   f) Therapy tolerance: pronounced stomatitis
8.) Preceding and concomitant diseases: none
9.) Accompanying therapy during chemolselenium therapy: none
10.) Survival status: dead
   Date of death: May 13, 1998;
   Cause of death: pancytopenia

What is claimed is:

1. A method of producing a synergistic cytotoxic effect on a cancer cell in a patient being treated for cancer, comprising contacting the cell with a cytostatic agent or a mixture of cytostatic agents that inhibits mitosis and simultaneously, separately or sequentially contacting the cell with at least one salt of $SeO_2$, by administering to the patient at least one salt of $SeO_2$ in a concentration of 0.1 mg/kg body weight of the patient to 1.25 mg/kg body weight of the patient, and the cytostatic agent in a concentration of 2 mg/m$^2$ body surface of the patient to 240 g/m$^2$ body surface of the patient, or by administering to the patient at least one salt of $SeO_2$ in a concentration of 0.1 mg/kg body weight of the patient to 0.3 mg/kg body weight of the patient, and the cytostatic agent in a concentration of 20 mg/m$^2$ body surface of the patient to 1000 mg/m$^2$ body surface of the patient, whereupon the synergistic cytotoxic effect of the cytostatic agent or the mixture of cytostatic agents and at least one salt of $SeO_2$ on the cell is produced wherein the cancer cell is sensitive to the cytostatic agent and the salt of SeO2.

2. The method of claim 1, wherein the cancer is large-cell bronchial carcinoma.

3. The method of claim 1, wherein the cancer is small-cell bronchial carcinoma.

4. The method of claim 1, wherein the cancer is adenocarcinoma.

5. The method of claim 1, wherein the cancer is pancreatic carcinoma.

6. The method of claim 1, wherein the cancer is prostatic carcinoma.

7. The method of claim 1, wherein the cancer is hypemephroma.

* * * * *